US010800718B2

(12) United States Patent
Detjen et al.

(10) Patent No.: US 10,800,718 B2
(45) Date of Patent: Oct. 13, 2020

(54) DISPROPORTIONATION AND TRANSALKYLATION OF HEAVY AROMATIC HYDROCARBONS (71) Applicant: ExxonMobil Chemical Patents Inc., Baytown, TX (US)

(72) Inventors: Todd E. Detjen, Houston, TX (US); Jeevan S. Abichandani, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/331,999

(22) PCT Filed: Feb. 10, 2017

(86) PCT No.: PCT/US2017/017303
§ 371 (c)(1),
(2) Date: Mar. 11, 2019

(87) PCT Pub. No.: WO2018/067193
PCT Pub. Date: Apr. 12, 2018

(65) Prior Publication Data
US 2019/0367431 A1 Dec. 5, 2019

Related U.S. Application Data (60) Provisional application No. 62/403,748, filed on Oct. 4, 2016.

(51) Int. Cl.
C07C 6/12 (2006.01)
B01J 29/80 (2006.01)
(Continued)

(52) U.S. Cl.
CPC .............. C07C 6/123 (2013.01); B01J 29/80 (2013.01); C07C 5/2732 (2013.01); C07C 6/126 (2013.01);
(Continued)

(58) Field of Classification Search
None
See application file for complete search history.

(56) References Cited

U.S. PATENT DOCUMENTS 4,642,406 A * 2/1987 Schmidt ................. C07C 6/123
585/475
5,030,786 A 7/1991 Shamshoum et al.
(Continued)

FOREIGN PATENT DOCUMENTS

EP 0202752 A 11/1986
EP 1094050 A 4/2001
(Continued)

OTHER PUBLICATIONS

Baerlocher et al. Atlas of Zeolite Framework Types Fifth Revised Edition. Elsevier on behalf of the Structure Commission of the IZA. (2001) pp. 183-184. (Year: 2001).*
(Continued)

Primary Examiner — In Suk C Bullock
Assistant Examiner — Alyssa L Cepluch (57) ABSTRACT Disclosed herein is a process for producing para-xylene comprising the steps of: (a) contacting a feedstock comprising toluene with a first catalyst under effective vapor phase toluene disproportionation conditions to disproportionate said toluene and produce a first product comprising benzene, unreacted toluene and greater than equilibrium amounts of para-xylene; and (b) contacting a feedstock comprising $C_{9+}$ aromatic hydrocarbons and benzene with a second catalyst in the presence of 0 wt. % or more of hydrogen having a 0
(Continued)

to 10 hydrogen/hydrocarbon molar ratio under effective $C_{9+}$ transalkylation conditions to transalkylate said $C_{9+}$ aromatic hydrocarbons and produce a second product comprising xylenes.

11 Claims, 2 Drawing Sheets

(51) Int. Cl.
    *C07C 5/27* (2006.01)
    *C07C 15/06* (2006.01)
    *C07C 15/08* (2006.01)
(52) U.S. Cl.
    CPC .............. *C07C 15/06* (2013.01); *C07C 15/08* (2013.01); *C07C 2529/44* (2013.01); *C07C 2529/74* (2013.01)

(56) References Cited

U.S. PATENT DOCUMENTS

| | | | |
|---|---|---|---|
| 5,081,323 A | 1/1992 | Innes et al. | |
| 5,659,098 A * | 8/1997 | Beck | B01J 29/40 585/467 |
| 5,763,720 A | 6/1998 | Buchanan et al. | |
| 5,942,651 A | 8/1999 | Beech, Jr. et al. | |
| 6,855,854 B1 | 2/2005 | James, Jr. | |
| 6,936,744 B1 | 8/2005 | Cheng et al. | |
| 6,958,425 B1 | 10/2005 | Bogdan et al. | |
| 7,241,930 B2 | 7/2007 | Schlosberg et al. | |
| 7,405,335 B1 * | 7/2008 | Casey | C07C 5/2702 585/319 |
| 7,553,791 B2 | 6/2009 | McMinn et al. | |
| 7,663,010 B2 | 2/2010 | Levin | |
| 8,163,966 B2 | 4/2012 | Levin | |
| 9,034,780 B2 | 5/2015 | Levin | |
| 2003/0130549 A1 | 7/2003 | Xie et al. | |
| 2005/0215839 A1 | 9/2005 | Bogdan et al. | |
| 2006/0138026 A1 | 6/2006 | Chen et al. | |
| 2008/0139859 A1 | 6/2008 | Clark et al. | |
| 2009/0112034 A1 | 4/2009 | Levin | |
| 2010/0228066 A1 | 9/2010 | Kong et al. | |
| 2010/0305379 A1 | 12/2010 | Riley et al. | |
| 2013/0259775 A1 | 10/2013 | Levin et al. | |
| 2013/0281750 A1 | 10/2013 | Abudawoud | |
| 2014/0243567 A1 | 8/2014 | Vincent et al. | |

FOREIGN PATENT DOCUMENTS

| | | |
|---|---|---|
| WO | 2010/065319 A | 6/2010 |
| WO | 2017/172067 A | 10/2017 |

OTHER PUBLICATIONS

Tsai, T-C, et al., "Metal Supported Zeolite for Heavy Aromatics Transalkylation Process", Catalysis Surveys from Asia, vol. 13, Issue 2, pp. 94-103, Jun. 2009.

Cavani, F. et al., "Liquid-phase transalkylation of diethylebenzenes with benzene over B-Zeolite: effect of operating parameters on the distribution of the products", Applied Catalysis A: General, vol. 226, Issues 1-2, pp. 31-40, Mar. 2002.

* cited by examiner

DISPROPORTIONATION AND TRANSALKYLATION OF HEAVY AROMATIC HYDROCARBONS

CROSS-REFERENCE OF RELATED APPLICATIONS

This application is a National Phase Application claiming priority to PCT Application Serial No. PCT/US2017/017303 filed Feb. 10, 2017, which claims priority to U.S. Provisional Application No. 62/403,748 filed Oct. 4, 2016 which are incorporated by reference in their entireties.

TECHNICAL FIELD

Processes are provided for the production of para-xylene by the selective disproportionation of toluene in the presence of a first catalyst, and the transalkylation of $C_{9+}$ aromatic hydrocarbons in the presence of a second catalyst.

BACKGROUND

Xylenes are important aromatic hydrocarbons, for which the worldwide demand is steadily increasing. The demand for xylenes, particularly para-xylene, has increased in proportion to the increase in demand for polyester fibers and film and typically grows at a rate of 5-7% per year. An important source of xylenes and other aromatic hydrocarbons is catalytic reformate, which is produced by contacting a mixture of petroleum naphtha and hydrogen with a strong hydrogenation/dehydrogenation catalyst, such as platinum, on a moderately acidic support, such as a halogen-treated alumina. The resulting reformate is a complex mixture of paraffins and the $C_6$ to $C_8$ aromatics, in addition to a significant quantity of heavier aromatic hydrocarbons. After removing the light ($C_{5-}$) paraffinic components, the remainder of the reformate is normally separated into $C_{7-}$, $C_8$ and $C_{9+}$-containing fractions using a plurality of distillation steps. The $C_8$-containing fraction is then fed to a xylene production loop where para-xylene is recovered, generally by adsorption or crystallization, and the resultant para-xylene depleted stream is subjected to catalytic conversion to isomerize the xylenes back towards equilibrium distribution and to reduce the level of ethylbenzene that would otherwise build up in the xylene production loop.

However, the quantity of xylene available from reformate $C_8$ fractions is limited and so recently refineries have also focused on the production of xylene by transalkylation of heavy ($C_{9+}$) aromatic hydrocarbons (both from reformate and other sources) with benzene and/or toluene over noble metal-containing zeolite catalysts. For example, U.S. Pat. No. 5,942,651 discloses a process for the transalkylation of heavy aromatics comprising contacting a feed comprising $C_{9+}$ aromatic hydrocarbons and toluene with a first catalyst composition comprising a molecular sieve having a constraint index ranging from 0.5 to 3, such as ZSM-12, and a hydrogenation component under transalkylation reaction conditions to produce a transalkylation reaction product comprising benzene and xylene. The transalkylation reaction product is then contacted with a second catalyst composition which comprises a molecular sieve having a constraint index ranging from 3 to 12, such as ZSM-5, and which may be in a separate bed or a separate reactor from the first catalyst composition, under conditions to remove benzene co-boilers in the product.

One problem associated with heavy aromatics transalkylation processes is catalyst aging since, as the catalyst loses activity with increasing time on stream, higher temperatures tend to be required to maintain constant conversion. When the maximum reactor temperature is reached, the catalyst needs to be replaced or regenerated, normally by oxidation. In particular, it has been found that the aging rate of existing transalkylation catalysts is strongly is dependent on the presence in the feed of aromatic compounds having alkyl substituents with two or more carbon atoms, such as ethyl and propyl groups. Thus these compounds tend to undergo reactions such as disproportionation and dealkylation/re-alkylation to produce $C_{10+}$ coke precursors.

To address the problem of $C_{9+}$ feeds containing high levels of ethyl and propyl substituents, U.S. Publication 2009/0112034 discloses a catalyst system adapted for transalkylation of a $C_{9+}$ aromatic feedstock with a $C_6$-$C_7$ aromatic feedstock comprising: (a) a first catalyst comprising a first molecular sieve having a Constraint Index in the range of 3-12 and 0.01 to 5 wt. % of at least one source of a first metal element of Groups 6-10; and (b) a second catalyst comprising a second molecular sieve having a Constraint Index less than 3 and 0 to 5 wt. % of at least one source of a second metal element of Groups 6-10, wherein the weight ratio of said first catalyst to said second catalyst is in the range of 5:95 to 75:25. The first catalyst, which is optimized for dealkylation of the ethyl and propyl groups in the feed, is located in front of the second catalyst, which is optimized for transalkylation, when they are brought into contact with a $C_{9+}$ aromatic feedstock and a $C_6$-$C_7$ aromatic feedstock in the presence of hydrogen.

However, despite these and other advances, there remains a number of unresolved problems with existing $C_{9+}$ aromatic conversion processes. One such problem is that the xylenes produced by the transalkylation step are in equilibrium concentration, in which the para-isomer generally comprises only about 22% of the total isomer mixture. Thus, maximizing para-xylene production requires circulation of large volumes of $C_8$ aromatics in the xylene production loop. In addition, xylene isomerization processes are generally limited by equilibrium constraints as to the per pass conversion of meta- and ortho-xylene to the desired para-isomer, again leading to process inefficiencies.

BRIEF SUMMARY

According to the present disclosure, it has now been found that the para-xylene yield and production efficiency in $C_{9+}$ aromatic hydrocarbon conversion processes can be improved by supplying fresh toluene to a disproportionation zone. By suitable selection of the disproportionation catalyst, the toluene can be selectively converted to para-xylene and benzene in the disproportionation reaction zone. After separation of the para-rich xylene fraction, the remaining benzene and toluene are recovered as a recycle benzene stream and/or a recycle toluene stream. A $C_{9+}$ aromatic hydrocarbon component is suppled to a liquid phase transalkylation zone, together with the recycle benzene stream and/or the recycle toluene stream to transalkylate the $C_{9+}$ aromatic hydrocarbon component to produce additional xylenes. Carrying out the transalkylation in the liquid phase allows for an improved lifetime for the catalysts used and/or an improved selectivity for production of aromatics having the desired number of carbons (such as $C_8$ aromatics) at lower severity reaction conditions while minimizing energy consumption.

Thus, in one aspect, the present disclosure relates to a process for producing xylene from $C_{9+}$ aromatic hydrocarbons. The process comprises a step (a) of contacting a first feedstock comprising toluene with a first catalyst in the presence of 0 wt. % or more of hydrogen under effective vapor phase toluene disproportionation conditions to disproportionate at least part of said toluene and produce a first product comprising para-xylene. The process also comprises a step (b) of contacting a second feedstock comprising aromatic hydrocarbons toluene with a second catalyst in the presence of 0 wt. % or more of hydrogen under effective liquid phase $C_{9+}$ transalkylation conditions to transalkylate at least part said $C_{9+}$ aromatic hydrocarbons and produce a second product comprising xylenes.

In a second aspect, the present disclosure relates to a process for producing xylene from $C_{9+}$ aromatic hydrocarbons comprising step (a) of contacting toluene with a first catalyst in the presence of 0 wt. % or more of hydrogen under effective vapor phase toluene disproportionation conditions to disproportionate at least part of the toluene and produce a first product comprising para-xylene, benzene and remaining toluene. In step (b), aromatic hydrocarbons and at least part of the benzene and/or toluene from the first product are contacted with a second catalyst in the presence of 0 wt. % or more of hydrogen under effective $C_{9+}$ transalkylation conditions. In this step, at least part of the $C_{9+}$ aromatic hydrocarbons are transalkylated to produce a second product comprising xylenes. In step (c), the para-xylene from at least the first product is separated. In a further step, additional para-xylene is separated from the second product.

In one or more embodiments, the separated xylene may then be supplied to a para-xylene recovery unit to recover para-xylene.

In one or more embodiments, the first catalyst comprises silica selectivated or carbon selectivated ZSM-5.

In one or more embodiments, the second catalyst comprises a molecular sieve having at least one of an MWW framework, a *BEA framework, a BEC framework, a FAU framework, or a MOR framework, or a mixture of two or more thereof.

DETAILED DESCRIPTION

Definitions and Overview

As used herein, the numbering scheme for the Periodic Table Groups is as described in Chemical and Engineering News, 63(5), 27 (1985).

As used in this specification, the term "framework type" is used in the sense described in the "Atlas of Zeolite Framework Types," 2001.

The term "aromatic" is used herein in accordance with its art-recognized scope which includes alkyl substituted and unsubstituted mono- and polynuclear compounds.

The term "catalyst" is used interchangeably with the term "catalyst composition".

The term "ethyl-aromatic compounds" means aromatic compounds having an ethyl group attached to the aromatic ring. The term "propyl-aromatic compounds" means aromatic compounds having a propyl group attached to the aromatic ring.

The term "$C_n$" hydrocarbon, wherein n is an positive integer, e.g., 1, 2, 3, 4, 5, 6, 7, 8, 9, 10, 11, 12, as used herein means a hydrocarbon having n number of carbon atom(s) per molecular. For example. $C_n$ aromatics means an aromatic hydrocarbon having n number of carbon atom(s) per molecule. The term "$C_{n+}$," hydrocarbon, wherein n is an positive integer, e.g., 1, 2, 3, 4, 5, 6, 7, 8, 9, 10, 11, 12, as used herein means a hydrocarbon having at least n number of carbon atom(s) per molecule. The term "$C_{n-}$" hydrocarbon, wherein n is an positive integer, e.g., 1, 2, 3, 4, 5, 6, 7, 8, 9, 10, 11, 12, as used herein means a hydrocarbon having no more than n number of carbon atom(s) per molecule.

The term "effective vapor phase toluene disproportionation conditions" means that the relevant reaction is conducted under conditions of temperature and pressure such that at least part of the aromatic components of the reaction mixture are in the vapor phase. In some embodiments, the mole fraction of the aromatic components in the vapor phase, relative to the total aromatics in the reaction mixture, can be at least 0.75, such as at least 0.85 or 0.95, up to 1 (all the aromatic components in the vapor phase).

The term "effective liquid phase $C_{9+}$ transalkylation conditions" means that the transalkylation reaction is conducted under conditions of temperature and pressure such that at least part of the aromatic components of the transalkylation reaction mixture are in the liquid phase. In some embodiments, the mole fraction of aromatic compounds in the liquid phase, relative to the total aromatics, can be at least 0.01, or at least 0.05, or at least 0.08, or at least 0.1, or at least 0.15, or at least 0.2, or at least 0.3, or at least 0.4, or at least 0.5, and optionally up to having substantially all aromatic compounds in the liquid phase.

The term "mordenite" as used herein includes, but is not limited to, a mordenite zeolite having a very small crystal size and having a high mesopore surface area made by the particular selection of the synthesis mixture composition, as disclosed in WO 2016/126431.

The term "xylenes" as used herein is intended to include a mixture of the isomers of xylene of ortho-xylene, meta-xylene and para-xylene.

Described herein are various processes for producing xylene from $C_{9+}$ aromatic hydrocarbons. In these processes, a first feedstock comprising toluene, normally fresh and/or recycle toluene, is contacted with a first catalyst in the presence of 0 wt. % or more of hydrogen under effective vapor phase toluene disproportionation conditions to disproportionate at least part of the toluene and produce a first product comprising para-xylene. A second feedstock comprising $C_{9+}$ aromatic hydrocarbons, normally fresh and/or recycle $C_{9+}$ aromatic hydrocarbons, together with benzene and/or toluene is then contacted with a second catalyst in the presence of 0 wt. % or more of hydrogen under effective liquid phase $C_{9+}$ transalkylation conditions to transalkylate at least part of the $C_{9+}$ aromatic hydrocarbons and produce a second product comprising xylenes, Para-xylene can be recovered from the first product and the second product.

Each of the first and second catalysts can be housed in a separate reactor or, where desired, two or more of the catalysts can be accommodated in the same reactor. For example, the first and second catalysts beds can be arranged in separate catalyst beds stacked one on top of the other in a single reactor.

Toluene Disproportionation Stage

In the first, toluene disproportionation stage of the present process, a first feedstock comprising toluene or toluene stream is contacted in the first reaction zone with a first catalyst composition comprising a first molecular sieve and optionally one or more hydrogenation components.

Examples of crystalline molecular sieves useful in the first catalyst composition include intermediate pore size zeolites, such as of ZSM-5, ZSM-11, ZSM-22, ZSM-23, ZSM-35, ZSM-48, ZSM-57 and ZSM-58. Also useful are silicoaluminophosphates (SAPO's), particularly SAPO-5 and SAPO-11 (U.S. Pat. No. 4,440,871) and aluminophosphates (ALPO$_4$'s), particularly ALPO$_4$-5, and ALPO$_4$-11 (U.S. Pat. No. 4,310,440). The entire contents of the above references are incorporated by reference herein. Preferred intermediate pore zeolites include ZSM-5, ZSM-11, ZSM-12, ZSM-35 and MCM-22. Most preferred is ZSM-5, preferably having a silica to alumina molar ratio of at least about 5, preferably at least about 10, more preferably at least 20.

Intermediate pore size molecular sieves useful in the toluene disproportionation stage are particularly those which have been modified to decrease their ortho-xylene sorption rate since these are found to be more selective for the production of para-xylene over the other xylene isomers. The desired decrease in ortho-xylene sorption rate can be achieved by subjecting the molecular sieve, in bound or unbound form, to selectivation, such as silicon selectivation, carbon selection (or coke) and others. Silicon selectivation through ex situ methods of impregnation or multiple impregnation or in situ methods of trim selectivation; or coke selectivation; or combination of these. Multiple impregnation methods are described, e.g., in U.S. Pat. Nos. 5,365,004; 5,367,099; 5,382,737; 5,403,800; 5,406,015; 5,476,823; 5,495,059; and 5,633,417. Other ex situ selectivations are described in U.S. Pat. Nos. 5,574,199 and 5,675,047. Trim selectivation is described, e.g., in U.S. Pat. Nos. 5,321,183; 5,349,113; 5,475,179; 5,498,814; and 5,607,888. Other silicon selectivations are described, e.g., in U.S. Pat. Nos. 5,243,117; 5,349,114; 5,365,003; 5,371,312; 5,455,213; 5,516,736; 5,541,146; 5,552,357; 5,567,666; 5,571,768; 5,602,066; 5,610,112; 5,612,270; 5,625,104; and 5,659,098. Coke selectivation is described in U.S. Pat. Nos. 5,234,875; 4,581,215; 4,508,836; 4,358,395; 4,117,026; and 4,097,543. All of these patents describing selectivation are incorporated by reference herein.

In particular, it has been found that the first catalyst composition should possess an equilibrium sorption capacity of xylene, which can be either para, meta, ortho or a mixture thereof, frequently para-xylene, since this isomer reaches equilibrium within the shortest time, of at least 1 gram per 100 grams of zeolite measured at 120° C. and a xylene pressure of 4.5±0.8 mm of mercury and an ortho-xylene sorption time for 30 percent of the xylene sorption capacity of greater than 50, preferably greater than 200, more preferably greater than 1200 (at the same conditions of temperature and pressure). The sorption measurements may be carried out gravimetrically in a thermal balance. The sorption test is described in U.S. Pat. Nos. 4,117,025; 4,159,282; 5,173,461; and Re. 31,782; each of which is incorporated by reference herein.

The first catalyst composition may include the first molecular sieve in bound or unbound form. Where a binder is used, a silica binder may be preferred. Procedures for preparing silica bound ZSM-5 are described in, for example, U.S. Pat. Nos. 4,582,815; 5,053,374; and 5,182,242, incorporated by reference herein. In some embodiments, a zeolite bound zeolite, as described in U.S. Pat. No. 5,665,325, may be employed in the first catalyst composition.

In addition to the molecular sieve described above, the first catalyst composition may include at least one hydrogenation component, such as at least one metal or compound thereof from Groups 4 to 13 of the Periodic Table of the Elements. Suitable metals include platinum, palladium, tin, silver, gold, copper, zinc, nickel, gallium, cobalt, molybdenum, rhodium, ruthenium, manganese, rhenium, tungsten, chromium, iridium, osmium, iron, cadmium, and mixtures (combinations) thereof. The metal may be added by cation exchange or by impregnation by known methods in amounts of from about 0.01% to about 10%, such as from 0.01% to about 5%, by weight of the catalyst.

Suitable conditions in the first reaction zone effective for accomplishing high para-xylene selectivity and acceptable toluene conversion levels include a reactor inlet temperature of from about 200° C. to about 550° C., preferably from about 300° C. to about 500° C.; a pressure from about atmospheric to about 5000 psig (100 to 34576 kPa-a), preferably about 20 to about 1000 psig (239 to 6996 kPa-a); a WHSV from about 0.1 to about 20, preferably from about 0.5 to about 10; and a H$_2$/hydrocarbon mole ratio from about 0 to about 20, preferably from about 0 to about 10. In particular, the conditions are generally selected so that at least the toluene is predominantly in the vapor phase. This process may be conducted in either continuous flow, batch or fluid bed operation. In some embodiments, the first reaction zone may be split between two or more separate reactors. In other embodiments, the first reaction zone and the second reaction zone, discussed below, may be housed in a single reactor.

Under the conditions in the first reaction zone, at least part of the toluene undergoes disproportionation into benzene and a para-xylene selective mixture of xylenes. Using the selectivated catalysts described above, the para-xylene content in the mixed xylenes may be of the order of 90%. As a result, the product exiting the first reaction zone is composed mainly of a para-xylene rich xylene mixture, benzene, lower alkanes and unreacted toluene. The disproportionation product is therefore sent to a separation system, normally a distillation train, where the product is separated into:

a gaseous mixture of lower alkanes which can be recovered for use as a fuel;

a benzene stream which is fed to a transalkylation reaction zone as described below;

an unreacted toluene stream which is at least partly recycled to the first reaction zone, but can also be fed to the transalkylation reaction zone as described below; and a para-xylene rich C$_8$ stream which is fed to a para-xylene recovery loop as described below.

C$_{9+}$ Aromatic Hydrocarbon Feedstock

The aromatic feed used in the present process comprises one or more aromatic hydrocarbons containing at least 9 carbon atoms. Specific C$_{9+}$ aromatic compounds found in a typical feed include mesitylene (1,3,5-trimethylbenzene), durene (1,2,4,5-tetramethylbenzene), hemimellitene (1,2,4-trimethylbenzene), pseudocumene (1,2,4-trimethylbenzene), 1,2-methylethylbenzene, 1,3-methylethylbenzene, 1,4-methylethylbenzene, propyl-substituted benzenes, butyl-substituted benzenes, and dimethylethylbenzenes. Suitable sources of the C$_{9+}$ aromatics are any C$_{9+}$ fraction from any refinery process that is rich in aromatics. This aromatics fraction may contain a substantial proportion of C$_{9+}$ aromatics, e.g., at least 50 wt. %, such as at least 80 wt. % C$_{9+}$ aromatics, wherein preferably at least 80 wt. %, and more preferably more than 90 wt. %, of the hydrocarbons will range from C$_9$ to C$_{12}$. Typical refinery fractions which may be useful include catalytic reformate, FCC naphtha or TCC naphtha.

Liquid Phase Transalkylation Stage

In the second, liquid phase transalkylation stage of the present process, a second feedstock comprising $C_{9+}$ aromatic hydrocarbon, and toluene and/or benzene, and optionally part of the benzene and/or toluene recovered from the disproportionation product, are contacted in a second liquid phase transalkylation reaction zone with a second catalyst composition comprising a second molecular sieve and optionally one or more hydrogenation components.

In one embodiment, a suitable molecular sieve for the second catalyst composition includes a molecular sieve with a framework structure having a 3-dimensional network of 12-member ring pore channels. Examples of framework structures having a 3-dimensional 12-member ring are the framework structures corresponding to faujasite (such as zeolite X or Y, including USY), *BEA (such as zeolite Beta), BEC (polymorph C of Beta), CIT-1 (CON), MCM-68 (MSE), hexagonal faujasite (EMT), ITQ-7 (ISV), ITQ-24 (IWR), and ITQ-27 (IWV), preferably faujasite, hexagonal faujasite, and Beta (including all polymorphs of Beta). It is noted that the materials having a framework structure including a 3-dimensional network of 12-member ring pore channels can correspond to zeolites, silicoaluminophosphates, aluminophosphates, and/or any other convenient combination of framework atoms.

Additionally or alternately, a suitable transalkylation catalyst includes a molecular sieve with a framework structure having a 1-dimensional network of 12-member ring pore channels, where the pore channel has a pore channel size of at least 6.0 Angstroms, or at least 6.3 Angstroms. The pore channel size of a pore channel is defined herein to refer to the maximum size sphere that can diffuse along a channel. Examples of framework structures having a 1-dimensional 12-member ring pore channel can include, but are not limited to, mordenite (MOR), zeolite L (LTL), and ZSM-18 (MEI). It is noted that the materials having a framework structure including a 1-dimensional network of 12-member ring pore channels can correspond to zeolites, silicoaluminophosphates, aluminophosphates, and/or any other convenient combination of framework atoms.

Additionally or alternately, a suitable transalkylation catalyst includes a molecular sieve having the MWW framework structure. Although the MWW framework structure does not have 12-member ring pore channels, the MWW framework structure does include surface sites that have features similar to a 12-member ring opening. Examples of molecular sieves having MWW framework structure include MCM-22, MCM-49, MCM-56, MCM-36, EMM-10, EMM-10-P, EMM-13, PSH-3, SSL-25, ERB-1, ITQ-1, ITQ-2, UZM-8, UZM-8HS, UZM-37, MIT-1, and interlayer expanded zeolites. It is noted that the materials having an MWW framework structure can correspond to zeolites, silicoaluminophosphates, aluminophosphates, and/or any other convenient combination of framework atoms.

Additionally or alternately, a suitable transalkylation catalyst includes an acidic microporous material that has a largest pore channel corresponding to a 12-member ring or larger, and/or that has a pore channel size of at least 6.0 Angstroms, or at least 6.3 Angstroms and/or that has another active surface having a size of at least 6.0 Angstroms. It is noted that such microporous materials can correspond to zeolites, silicoaluminophosphates, aluminophosphates, and/or materials that are different from molecular sieve type materials.

The molecular sieve can optionally be characterized based on having a composition with a molar ratio $YO_2$ over $X_2O_3$ equal to n, wherein X is a trivalent element, such as aluminum, boron, iron, indium and/or gallium, preferably aluminum and/or gallium, and Y is a tetravalent element, such as silicon, tin and/or germanium, preferably silicon. For example, when Y is silicon and X is aluminum, the molar ratio of $YO_2$ over $X_2O_3$ is the silica-to-alumina molar ratio. For a MWW framework molecular sieve, n can be less than about 50, e.g., from about 2 to less than about 50, usually from about 10 to less than about 50, more usually from about 15 to about 40. For a molecular sieve having the framework structure of Beta and/or its polymorphs, n can be about 10 to about 60, or about 10 to about 50, or about 10 to about 40, or about 20 to about 60, or about 20 to about 50, or about 20 to about 40, or about 60 to about 250, or about 80 to about 250, or about 80 to about 220, or about 10 to about 400, or about 10 to about 250, or about 60 to about 400, or about 80 to about 400. For a molecular sieve having the framework structure FAU, n can be about 2 to about 400, or about 2 to about 100, or about 2 to about 80, or about 5 to about 400, or about 5 to about 100, or about 5 to about 80, or about 10 to about 400, or about 10 to about 100, or about 10 to about 80. Optionally, the above n values can correspond to n values for a ratio of silica to alumina in the MWW, *BEA, and/or FAU framework molecular sieve. In such optional aspects, the molecular sieve can optionally correspond to an aluminosilicate and/or a zeolite.

Optionally, the catalyst comprises 0.01 wt. % to 5.0 wt. %, or 0.01 wt. % to 2.0 wt. %, or 0.01 wt. % to 1.0 wt. %, or 0.05 wt. % to 5.0 wt. %, or 0.05 wt. % to 2.0 wt. %, or 0.05 wt. % to 1.0 wt. %, or 0.1 wt. % to 5.0 wt. %, or 0.1 to 2.0 wt. %, or 0.1 wt. % to 1.0 wt. %, of a metal element of Groups 5-11 (according to the IUPAC Periodic Table). The metal element may be at least one hydrogenation component, such as one or more metals selected from Group 5-11 and 14 of the Periodic Table of the Elements, or a mixture of such metals, such as a bimetallic (or other multimetallic) hydrogenation component. Optionally, the metal can be selected from Groups 8-10, such as a Group 8-10 noble metal. Specific examples of useful metals are iron, tungsten, vanadium, molybdenum, rhenium, chromium, manganese, ruthenium, osmium, nickel, cobalt, rhodium, iridium, copper, tin, noble metals such as platinum or palladium, and combinations thereof. Specific examples of useful bimetallic combinations (or multimetallic combinations) are those where Pt is one of the metals, such as Pt/Sn, Pt/Pd, Pt/Cu, and Pt/Rh. In some aspects, the hydrogenation component is palladium, platinum, rhodium, copper, tin, or a combination thereof. The amount of the hydrogenation component can be selected according to a balance between hydrogenation activity and catalytic functionality. For a hydrogenation component including two or more metals (such as a bimetallic hydrogenation component), the ratio of a first metal to a second metal can range from 1:1 to about 1:100 or more, preferably 1:1 to 1:10.

Optionally, a suitable transalkylation catalyst can be a molecular sieve that has a constraint index of 1-12, optionally but preferably less than 3. The constraint index can be determined by the method described in U.S. Pat. No. 4,016,218, which is incorporated herein by reference with regard to the details of determining a constraint index.

Additionally or alternately, a transalkylation catalyst (such as a transalkylation catalyst system) can be used that has a reduced or minimized activity for dealkylation. The Alpha value of a catalyst can provide an indication of the activity of a catalyst for dealkylation. In various aspects, the transalkylation catalyst can have an Alpha value of about 100 or less, or about 50 or less, or about 20 or less, or about 10 or less, or about 1 or less. The alpha value test is a measure of the cracking activity of a catalyst and is described in U.S. Pat. No. 3,354,078 and in the Journal of Catalysis, Vol. 4, p. 527 (1965); Vol, 6, p. 278 (1966); and Vol, 61, p. 395 (1980), each incorporated herein by reference as to that description. The experimental conditions of the test used herein include a constant temperature of 538° C. and a variable flow rate as described in detail in the Journal of Catalysis, Vol. 61, p. 395.

In addition to the second molecular sieve, it may be desirable to incorporate in the second catalyst composition another material that is resistant to the temperatures and other conditions employed in the transalkylation process of the disclosure. Such materials include active and inactive materials and synthetic or naturally occurring zeolites, as well as inorganic materials such as clays, silica, hydrotalcites, perovskites, spinels, inverse spinels, mixed metal oxides, and/or metal oxides such as alumina, lanthanum oxide, cerium oxide, zirconium oxide, and titania. The inorganic material may be either naturally occurring, or in the form of gelatinous precipitates or gels including mixtures of silica and metal oxides.

Use of a material in conjunction with each molecular sieve, i.e., combined therewith or present during its synthesis, which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may be incorporated into, for example, alumina, to improve the crush strength of the catalyst composition under commercial operating conditions. It is desirable to provide a catalyst composition having good crush strength because in commercial use, it is desirable to prevent the catalyst composition from breaking down into powder-like materials.

Naturally occurring clays that can be composited with each molecular sieve as a binder for the catalyst composition include the montmorillonite and kaolin family, which families include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, each molecular sieve (and/or other microporous material) can be composited with a binder or matrix material, such as an inorganic oxide selected from the group consisting of silica, alumina, zirconia, titania, thoria, beryllia, magnesia, lanthanum oxide, cerium oxide, manganese oxide, yttrium oxide, calcium oxide, hydrotalcites, perovskites, spinels, inverse spinels, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form so as to facilitate extrusion of the catalyst composition.

In some aspects, a molecular sieve (and/or other microporous material) can be used without an additional matrix or binder. In other aspects, a molecular sieve/microporous material can be admixed with a binder or matrix material so that the final catalyst composition contains the binder or matrix material in an amount ranging from 5 to 95 wt. %, and typically from 10 to 60 wt. %.

Prior to use, steam treatment of the catalyst composition may be employed to minimize the aromatic hydrogenation activity of the catalyst composition. In the steaming process, the catalyst composition is usually contacted with from 5 to 100% steam, at a temperature of at least 260° C. to 650° C. for at least one hour, specifically 1 to 20 hours, at a pressure of 100 to 2590 kPa-a.

A hydrogenation component can be incorporated into the catalyst composition by any convenient method. Such incorporation methods can include co-crystallization, exchange into the catalyst composition, liquid phase and/or vapor phase impregnation, or mixing with the molecular sieve and binder, and combinations thereof. For example, in the case of platinum, a platinum hydrogenation component can be incorporated into the catalyst by treating the molecular sieve with a solution containing a platinum metal-containing ion. Suitable platinum compounds for impregnating the catalyst with platinum include chloroplatinic acid, platinous chloride and various compounds containing the platinum ammine complex, such as $Pt(NH_3)_4Cl_2 \cdot H_2O$ or $(NH_3)_4Pt(NO_3)_2 \cdot H_2O$. Palladium can be impregnated on a catalyst in a similar manner.

Alternatively, a compound of the hydrogenation component may be added to the molecular sieve when it is being composited with a binder, or after the molecular sieve and binder have been formed into particles by extrusion or pelletizing. Still another option can be to use a binder that is a hydrogenation component and/or that includes a hydrogenation component.

After treatment with the hydrogenation component, the catalyst is usually dried by heating at a temperature of 65° C. to 160° C., typically 110° C. to 143° C., for at least 1 minute and generally not longer than 24 hours, at pressures ranging from 100 to 200 kPa-a. Thereafter, the molecular sieve may be calcified. In a stream of dry gas, such as air or nitrogen, at temperatures of from 260° C. to 650° C. for 1 to 20 hours, Calcination is typically conducted at pressures ranging from 100 to 300 kPa-a.

In addition, prior to contacting the catalyst composition with the hydrocarbon feed, the hydrogenation component can optionally be sulfided. This is conveniently accomplished by contacting the catalyst with a source of sulfur, such as hydrogen sulfide, at a temperature ranging from about 320° C. to 480° C. The source of sulfur can be contacted with the catalyst via a carrier gas, such as hydrogen or nitrogen. Sulfiding per se is known and sulfiding of the hydrogenation component can be accomplished without more than routine experimentation by one of ordinary skill in the art in possession of the present disclosure.

Generally, the conditions employed in a liquid phase transalkylation process can include a temperature of about 400° C. or less, or about 360° C. or less, or about 320° C. or less, and/or at least about 100° C., or at least about 200° C. such as between 100° C. to 400° C. or 100° C. to 340° C., or 230° C. to 300° C.; a pressure of 2.0 MPa-g to 10.0 MPa-g, or 3.0 MPa-g to 8.0 MPa-g, or 3.5 MPa-g to 6.0 MPa-g; an $H_2$:hydrocarbon molar ratio of 0 to 20, or 0.01 to 20, or 0.1 to 10; and a weight hourly space velocity ("WHSV") for total hydrocarbon feed to the reactor(s) of 0.1 to 100 $hr^{-1}$, or 1 to 20 $hr^{-1}$. Optionally, the pressure during transalkylation can be at least 4.0 MPa-g. It is noted that $H_2$ is not necessarily required during the reaction, so optionally the transalkylation can be performed without introduction of $H_2$. The feed can be exposed to the transalkylation catalyst under fixed bed conditions, fluidized bed conditions, or other conditions that are suitable when a substantial liquid phase is present in the reaction environment.

Figure 1:
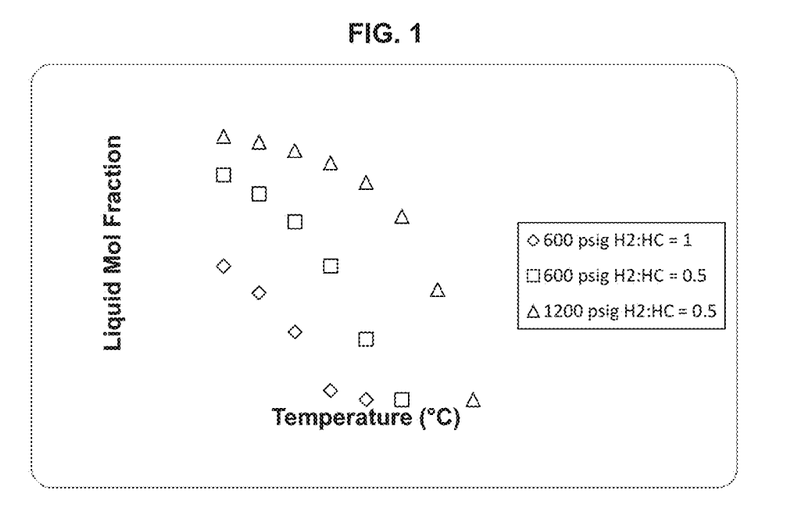
FIG. 1 shows examples of the mole fraction of a feed in the liquid phase at various temperature and pressure conditions.

In addition to staying within the general conditions above, the transalkylation conditions can be selected so that a desired amount of the hydrocarbons (reactants and products) in the reactor are in the liquid phase. Referring now to FIG. 1, where it shows calculations for the amount of liquid that should be present for a feed corresponding to a 1:1 mixture of toluene and mesitylene at several conditions that are believed to be representative of potential transalkylation conditions. The calculations in FIG. 1 show the mole fraction that is in the liquid phase as a function of temperature. The three separate groups of calculations shown in FIG. 1 correspond to a vessel containing a specified pressure based on introducing specified relative molar volumes of the toluene/mesitylene feed and $H_2$ into the reactor. One data set corresponds to a 1:1 molar ratio of toluene/mesitylene feed and $H_2$ at 600 psig (~4 MPa-g). A second data set corresponds to a 2:1 molar ratio of toluene/mesitylene teed and $H_2$ at 600 psig (~4 MPa-g). A third data set corresponds to a 2:1 molar ratio of toluene/mesitylene feed and $H_2$ at 1200 psig (~8 MPa-g).

As shown in FIG. 1, temperatures below about 260° C. can lead to formation of a substantial liquid phase (liquid mole fraction of at least 0.1) under all of the calculated conditions, including the combination of the lower pressure (600 psig) and the lower ratio of feed to hydrogen (1:1) shown in FIG. 1. It is noted that based on a ratio of feed to hydrogen of 1:1, a total pressure of 600 psig corresponds to partial pressure of aromatic feed of about 300 psig. Higher temperatures up to about 320° C. can also have a liquid phase (at least 0.01 mole fraction), depending on the pressure and relative amounts of reactants in the environment. More generally, temperatures such as up to 360° C. or up to 400° C. or greater can also be used for liquid phase transalkylation, so long as the combination of temperature and pressure in the reaction environment can result in a liquid mole fraction of at least 0.01. It is noted that conventional transalkylation conditions typically involve temperatures greater than 350° C. and/or pressures below 4 MPag, but such conventional transalkylation conditions do not include a combination of pressure and temperature that results in a liquid mole fraction of at least 0.01.

The resulting effluent from the liquid phase transalkylation process can have a to xylene yield, relative to the total weight of the hydrocarbons in the effluent, of at least about 4 wt. %, or at least about 6 wt. %, or at least about 8 wt. %, or at least about 10 wt. %. Other major components of the transalkylation effluent include benzene, toluene and residual $C_{9+}$ aromatic hydrocarbons. Separation of these components can be achieved using the same or a different separation system as that used to separate the products of the toluene disproportionation stage. In particular, the xylene can be recovered and supplied to a para-xylene recovery loop, while the benzene and residual $C_{9+}$ aromatic hydrocarbons can be recycled to the liquid phase transalkylation reactor and the toluene can be removed and either recycled to disproportionation or liquid phase transalkylation or both.

Figure 2:
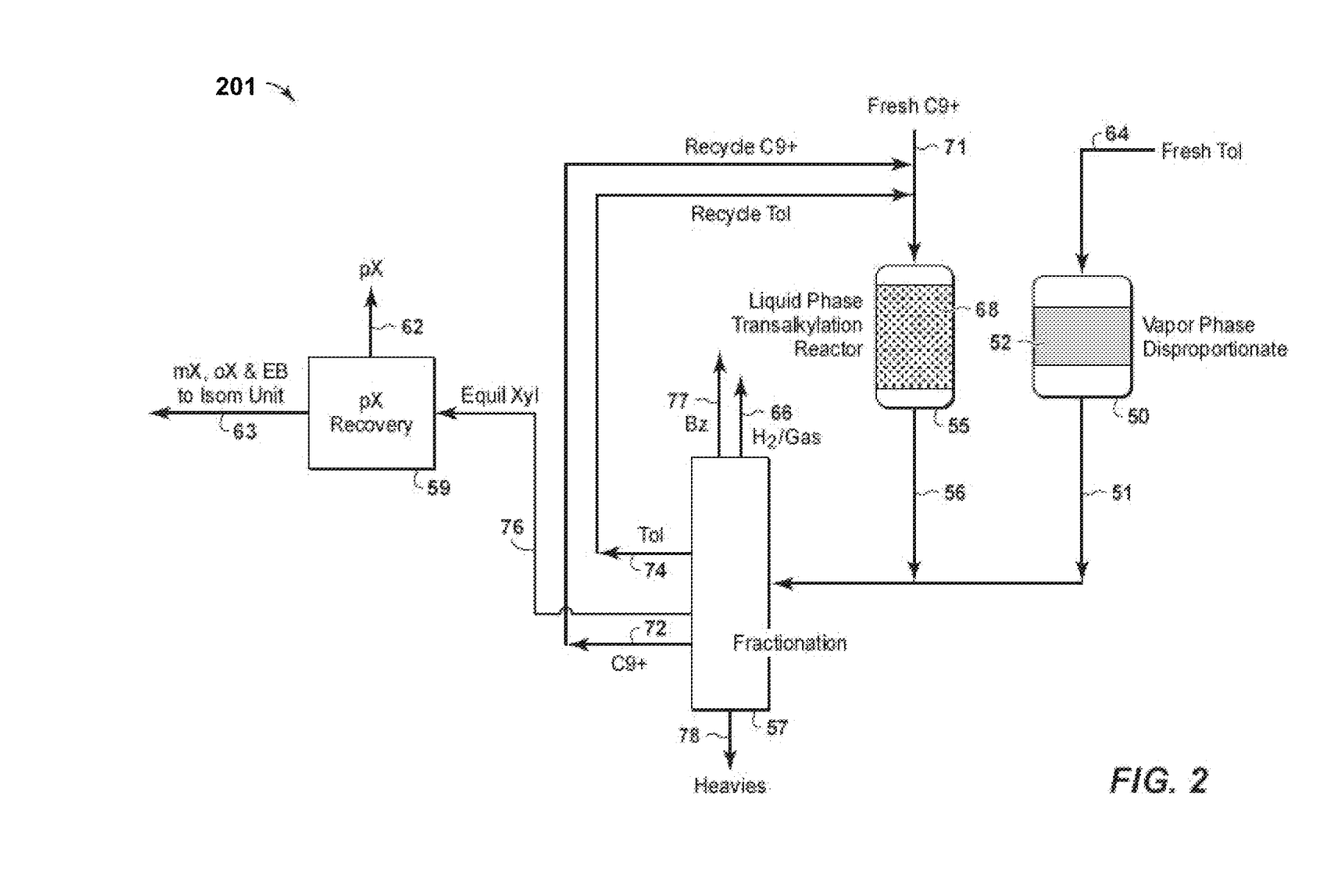
FIG. 2 is a flow diagram of a $C_{9+}$ aromatic hydrocarbon transalkylation process according to at least one embodiment of the present disclosure.

Referring now to FIG. 2, one embodiment 201 of the present process for producing xylenes, and particularly para-xylenes, from $C_{9+}$ aromatic hydrocarbons is shown. Fresh toluene feed (and optionally recycle toluene, not shown) is supplied by line 64 to a vapor phase disproportionation reaction zone 50, which optionally receives a supply of hydrogen (not shown). The disproportionation reaction zone 50 houses a first catalyst composition 52 comprising a molecular sieve having an intermediate pore size, such as, for example, ZSM-5. The molecular sieve may be selectivated with silicon or carbon, and contains a optionally hydrogenation metal, such as, for example, platinum. The disproportionation reaction zone 50 is operated under vapor phase disproportionation conditions such that at least some of the toluene is disproportionated to produce a first product comprising xylene, benzene and unreacted toluene. The xylene produced has greater than equilibrium amounts of para-xylene together with less than equilibrium amounts of the ortho-xylene and meta-xylene isomers.

The effluent from the disproportionation reaction zone 50 is collected in line 51 and fed to a fractionation system 57, where the light gases, including hydrogen, are removed via line 66 and the benzene is removed via line 77. The $C_{9+}$ aromatic hydrocarbons are collected in line 72 and fed to a transalkylation reaction zone 55. In some embodiments (not shown), part of the benzene removed via line 77 is also fed to the transalkylation reaction zone 55 as recycle benzene. In addition, the residual toluene is removed via line 74 as feed to the transalkylation reaction zone 55, or as recycle to the disproportionation reaction zone 50 (not shown). The para-xylene rich $C_8$ component is separated in the fractionation system 57 via line 76 for recovery of the desired para-xylene product. Heavies are recovered in line 78 for recovery as fuel value or for another use.

The transalkylation reaction zone 55 houses a second catalyst 68 composition comprising a molecular sieve. The molecular sieve has a constraint index of 1-12, preferably, a constraint index of less than 3, such as, for example, beta or MCM-49, and a hydrogenation component, such as, for example, platinum or palladium. The transalkylation reaction zone 55 is maintained under at least partial liquid phase or liquid phase conditions effective for transalkylation of the fresh $C_{9+}$ aromatic hydrocarbons supplied by line 71 and recycle $C_{9+}$ aromatic hydrocarbons supplied via line 72 along with at least part of the recycle toluene supplied via line 74 to produce a mixture including an equilibrium mixture of xylene isomers. Optionally, fresh toluene (not shown) may be supplied to transalkylation reactor 55 along with the recycle toluene via line 74. The effluent from the transalkylation reaction zone 55 is collected in line 56 and fed to the fractionation system 57, typically after combination with the effluent from the disproportionation reaction zone 50 in line 51.

The para-xylene rich $C_8$ stream collected in line 76 typically has from above equilibrium amounts of para-xylene (above 24 wt. %) up to about 60 wt. %. This para-xylene rich $C_8$ stream is initially supplied to a para-xylene recovery unit 59, such as, for example, a para-xylene extraction unit or a simulated moving bed column (SMB) 25, where the para-xylene is selectively adsorbed and, after treatment with a suitable desorbant, such as for example paradiethylbenzene, paradifluorobenzene, diethylbenzene or toluene or mixtures thereof, is recovered via line 62 for further purification. After separation of the para-xylene, the remaining para-xylene depleted steam, which comprises meta-xylene, ortho-xylene and ethylbenzene, is fed by line 63 to a xylene isomerization section (not shown) which can be operated in the gas phase or the liquid phase to return the xylenes in para-xylene depleted steam back to equilibrium concentration before the isomerized stream is recycled back to the SMB 25.

While particular embodiments have been described and illustrated, those of ordinary skill in the art will appreciate that this disclosure lends itself to variations not necessarily illustrated herein. For this reason, then, reference should be made solely to the appended claims for purposes of determining the scope of the present invention.

All patents, patent applications, test procedures, priority documents, articles, publications, manuals, and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated.

While the illustrative embodiments have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty, including all features which would be treated as equivalents thereof by those having ordinary skill in the art.

What is claimed is:

1. A process for producing xylene from $C_{9+}$ aromatic hydrocarbons, the process comprising:
   (a) contacting toluene with a first catalyst in the presence of 0 wt. % or more of hydrogen under effective vapor phase toluene disproportionation conditions to disproportionate at least part of the toluene and produce a first product comprising para-xylene, benzene and remaining toluene;
   (b) contacting $C_{9+}$ aromatic hydrocarbons and at least part of the benzene and/or toluene from the first product with a second catalyst in the presence of 0 wt. % or more of hydrogen under effective $C_{9+}$ transalkylation conditions to transalkylate at least part of the $C_{9+}$ aromatic hydrocarbons and produce a second product comprising xylenes, wherein a portion of the first product is supplied to the contacting in (b) without intermediate separation; and
   (c) separating para-xylene from a portion of the first product.

2. The process of claim 1, wherein the contacting in (b) is conducted under liquid phase $C_{9+}$ transalkylation conditions.

3. The process of claim 1, further comprising separating benzene from a portion of the first product and supplying at least part of the separated benzene to the contacting in (b).

4. The process of claim 1, further comprising:
   (d) separating the remaining toluene from a portion of the first product; and
   (e) supplying at least part of the separated toluene to the contacting in (b) or recycling the separated toluene to contacting in (a).

5. The process of claim 1, further comprising separating para-xylene from a portion of the first product and the second product.

6. The process of claim 1, wherein the first catalyst comprises selectivated ZSM-5.

7. The process of claim 6, wherein the selectivated ZSM-5 is silicon selectivated ZSM-5 or carbon selectivated ZSM-5.

8. The process of claim 7, wherein the first catalyst further comprises 0.01 wt. % to 5 wt. % of a metal selected from the group consisting of Pd, Pt, Ni, Rh, Sn, and a combination of two or more thereof.

9. The process of claim 1, wherein the second catalyst comprises a molecular sieve having at least one of an MWW framework, a *BEA framework, a BEC framework, a FAU framework, or a MOR framework, or a mixture of two or more thereof.

10. The process of claim 9, wherein the second catalyst comprises a molecular sieve having an MWW framework type selected from the group consisting of MCM-22, MCM-36, MCM-49, MCM-56, SSZ-25, MIT-1, EMM-10, EMM-10-P, EMM-12, EMM-13, ITQ-1, ITQ-2, ITQ-30, UZM-8, UZM-8HS, UZM-37, and mixtures of two or more thereof.

11. The process of claim 9, wherein the second catalyst further comprises 0.01 wt. % to 5 wt. % of a metal selected from the group consisting of Pd, Pt, Ni, Rh, Sn, and a combination of two or more thereof.

* * * * *